United States Patent [19]

Murayama et al.

[11] 4,007,158
[45] Feb. 8, 1977

[54] NOVEL PIPERIDINE DERIVATIVES FOR THE STABILIZATION OF SYNTHETIC POLYMERS

[75] Inventors: Keisuke Murayama; Syoji Morimura; Takao Yoshioka; Toshimasa Toda; Eiko Mori; Hideo Horiuchi; Susumu Higashida; Katsuaki Matsui; Tomoyuki Kurumada; Noriyuki Ohta; Hisayou Osawa, all of Tokyo, Japan

[73] Assignee: Sankyo Company Limited, Tokyo, Japan

[22] Filed: July 3, 1974

[21] Appl. No.: 485,567

[30] Foreign Application Priority Data

July 20, 1973 Japan .............................. 48-81369

[52] U.S. Cl. ...................................... 260/45.8 NZ
[51] Int. Cl.² ...................................... C08K 5/00
[58] Field of Search ............... 260/45.8 NZ, 45.8 A

[56] References Cited

UNITED STATES PATENTS

| | | | |
|---|---|---|---|
| 3,660,331 | 5/1972 | Ludwig | 260/45.8 A |
| 3,692,778 | 9/1972 | Murayama et al. | 260/45.8 NZ |
| 3,790,525 | 2/1974 | Murayama et al. | 260/45.8 NZ |
| 3,839,273 | 10/1974 | Murayama et al. | 260/45.8 NZ |
| 3,859,293 | 1/1975 | Murayama et al. | 260/45.8 NZ |

Primary Examiner—M. J. Welsh
Attorney, Agent, or Firm—Toren, McGeady and Stanger

[57] ABSTRACT

Novel piperidine derivatives of formula:

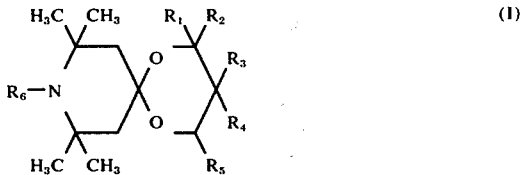

(wherein 2 or 3 of $R_1$, $R_2$, $R_3$, $R_4$ and $R_5$ represent alkyl groups having from 1 to 4 carbon atoms and the remainder of $R_1$, $R_2$, $R_3$, $R_4$ and $R_5$ are hydrogen atoms, and $R_6$ represents a hydrogen atom, an alkyl group, an alkenyl group, an alkynyl group, a substituted alkyl group, an aliphatic acyl group, an alkoxycarbonyl group or an aralkoxycarbonyl group) are useful as stabilizers for synthetic polymers.

6 Claims, No Drawings

NOVEL PIPERIDINE DERIVATIVES FOR THE STABILIZATION OF SYNTHETIC POLYMERS

BACKGROUND OF THE INVENTION

The invention relates to a new class of piperidine derivatives and to the use of these piperidine derivatives as stabilizers for synthetic polymers.

The excellent properties and wide variability in the obtainable properties of synthetic polymers have resulted in their widespread and increasing use throughout the world in various forms, for example as filaments, fibers, yarns, films, sheets, other molded forms, latexes and foams. However, the majority of the common synthetic polymers suffer from poor thermal- and photo-stability. For example, polyolefins and polyurethane elastomers frequently undergo severe deterioration when exposed to sunlight or ultraviolet radiation; polyvinyl chloride and polyvinylidene chloride can be degraded and discolored by the action of light and heat; with the elimination of hydrogen chloride; and polyamides are also frequently subject to photo-deterioration. Various stabilizers have been used in the past to overcome these difficulties, examples including: benzotriazole and benzophenone derivatives for polyolefins; phenolic compounds and benzophenone derivatives for polyurethanes; and lead salts (e.g. basic lead silicate and tribasic lead maleate) or organotin compounds (e.g. dibutyltin laurate and dibutyltin maleate) for polyvinyl chloride and polyvinylidene chloride. However, many problems still remain and thus there is still a need for effective stabilizers.

BRIEF SUMMARY OF INVENTION

It is accordingly an object of the invention to provide new piperidine derivatives which are effective stabilizers for synthetic polymers.

It is a further object of the invention to provide compositions of matter comprising at least one synthetic polymer in admixture with an effective stabilizing amount of at least one of the piperidine derivatives of the invention.

Other objects and advantages of the invention will become apparent as the description proceeds.

The piperidine derivatives of the invention are compounds having the formula:

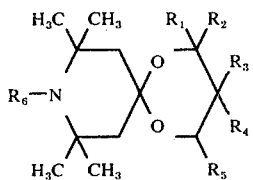

wherein:

2 or 3 of $R_1$, $R_2$, $R_3$, $R_4$ and $R_5$ represent alkyl groups having from 1 to 4 carbon atoms, the remainder of $R_1$, $R_2$, $R_3$, $R_4$ and $R_5$ being hydrogen atoms; and $R_6$ represents a substituent selected from the group consisting of: a hydrogen atom; alkyl groups; alkenyl groups; alkynyl groups; aralkyl groups; hydroxyalkyl groups; alkoxyalkyl groups; aliphatic or aromatic acyloxyalkyl groups; cyanoalkyl groups; haloalkyl groups; epoxyalkyl groups; alkoxycarbonylalkyl groups; aliphatic acyl groups; alkoxycarbonyl groups; and aralkoxycarbonyl groups.

DETAILED DESCRIPTION OF INVENTION

In accordance with the invention, it has now been discovered that the piperidine derivatives of formula (I) can effectively stabilize a wide range of synthetic polymers against photo- and thermal-deterioration.

In the foregoing formula (I), when $R_1$, $R_2$, $R_3$, $R_4$ or $R_5$ is an alkyl group, it may be a methyl, ethyl, n-propyl, isopropyl or isobutyl group, and 2 or 3 of $R_1$, $R_2$, $R_3$, $R_4$ and $R_5$ must be such an alkyl group. Preferred combinations of $R_1$, $R_2$, $R_3$, $R_4$ and $R_5$ are as follows:

(a) each of $R_1$, $R_2$ and $R_4$ represents a hydrogen atom and $R_3$ and $R_5$ are each an alkyl group having from 1 tp 4 carbon atoms, (b) each of $R_1$, $R_2$ and $R_5$ represents a hydrogen atom and each of $R_3$ and $R_4$ represents an alkyl group having from 1 to 4 carbon atoms, (c) each of $R_1$ and $R_2$ represents a hydrogen atom and each of $R_3$, $R_4$ and $R_5$ represents an alkyl group having from 1 to 4 carbon atoms, and (d) each of $R_3$ and $R_4$ represents a hydrogen atom and each of $R_1$, $R_2$ and $R_5$ represents an alkyl group having from 1 to 4 carbon atoms.

$R_6$ is preferably one of the following: a hydrogen atom; an alkyl group having from 1 to 8, preferably from 1 to 4 carbon atoms, for example a methyl, ethyl, n-propyl, isopropyl, butyl or octyl group, most preferably a methyl group; an alkenyl group having 3 or 4 carbon atoms, preferably an allyl group; an alkynyl group having 3 or 4 carbon atoms, for example a 2-propynyl group; an aralkyl group, preferably, a benzyl group; a hydroxyalkyl group having from 1 to 3 carbon atoms in its alkyl moiety, preferably a 2-hydroxyethyl group; an alkoxyalkyl group having from 1 to 4 carbon atoms in its alkoxy moiety and from 1 to 3 carbon atoms in its alkyl moiety, for example a 2-methoxyethyl, 2-ethoxyethyl or ethoxymethyl group; an aliphatic acyloxyalkyl group whose alkyl moiety has from 1 to 3, preferably 2 carbon atoms and in which the acyl moiety, if saturated, has from 1 to 18, preferably 2 to 4 carbon atoms or, if unsaturated, has from 3 to 6 preferably 3 or 4 carbon atoms, for example a 2-acetoxyethyl, 2-butyryloxyethyl, 2-octanoyloxyethyl, 2-stearoyloxyethyl, 2-methacryloyloxyethyl, 2-acryloyloxyethyl, 2-crotonoyloxyethyl or 2-sorboyloxyethyl group; an aromatic acyloxyalkyl group having from 1 to 3 preferably 2 carbon atoms in its alkyl moiety and whose acyl moiety is a benzoyl group optionally substituted with alkyl group having from 1 to 4 carbon atoms and/or a hydroxy group, for example, a 2-benzoyloxyethyl, 2-m-toluoyloxyethyl, 2-p-tert-butylbenzoyloxyethyl or salicyloyloxyethyl group; a cyanoalkyl group having from 1 to 3 carbon atoms in the alkyl moiety, for example, a cyanomethyl or 2-cyanoethyl group; a haloalkyl group having from 1 to 3 carbon atoms in its alkyl moiety, for example, a 2-chloroethyl group; an epoxyalkyl group preferably a 2, 3-epoxypropyl group; an alkoxycarbonylalkyl group having from 1 to 8 carbon atoms in the alkoxy moiety and from 1 to 3 carbon atoms in the alkyl moiety, for example, an ethoxycarbonylmethyl, butoxycarbonyl, methyl, octoxycarbonylmethyl, 2-methoxycarbonylethyl or methoxycarbonylmethyl group, most preferably an alkoxycarbonylmethyl group; an aliphatic acyl group in which the acyl moiety, if saturated, has from 2 to 8, preferably from 2 to 4 carbon atoms or, if unsaturated, has 3 or 4 carbon atoms, e.g., an acetyl, acryloyl, propionyl, butyryl or crotanyl group; an alkoxycarbonyl group having from 2 to 5 carbon atoms, e.g., a butoxycarbonyl, ethoxycarbonyl or octoxycarbonyl group; or an aralkoxycarbonyl group, for example a benzyloxycarbonyl group.

We particularly prefer that $R_6$ should be: a hydrogen atom; an alkyl group having from 1 to 4 carbon atoms; an allyl group; a benzyl group; a 2-hydroxyethyl group; an alkoxycarbonylmethyl group having from 1 to 4 carbon atoms in its alkoxy moiety; a 2,3-epoxypropyl group; a saturated aliphatic acyloxyethyl group having from 2 to 4 carbon atoms in its acyl moiety; a 2-benzoyloxyethyl group or a saturated aliphatic acyl group having from 2 to 4 carbon atoms. A hydrogen atom, a methyl group or a 2-hydroxyethyl group is most preferred.

The following is a non-limiting list of individual piperidine derivatives of formula (I). The numbers appended to the compounds in this list will be used to identify them hereinafter in the Examples.

(1) 9-Aza-3,3,8,8,10,10-hexamethyl-1,5-dioxaspiro[5.5]undecane.
(2) 9-Aza-2,4,4,8,8,10,10-heptamethyl-1,5-dioxaspiro[5.5]undecane.
(3) 9-Aza-3,8,8,10,10-pentamethyl-1,5-dioxa-3-propylspiro[5.5]undecane.
(4) 9-Aza-2-isopropyl-3,3,8,8,10,10-hexamethyl-1,5-dioxaspiro[5.5]undecane.
(5) 9-Aza-3-ethyl-8,8,10,10-tetramethyl-1, 5-dioxa-2-propylspiro[5.5]undecane.
(6) 9-Aza-3,3,8,8,9,10,10-heptamethyl-1,5-dioxaspiro[5.5]undecane.
(7) 9-Aza-2,4,4,8,8,9,10,10-octamethyl-1,5-dioxaspiro[5.5]undecane.
(8) 9-Aza-3-ethyl-8,8,9,10,10-pentamethyl-1,5-dioxa-2-propylspiro[5.5]undecane.
(9) 9Allyl-9-aza-3,3,8,8,10,10-hexamethyl-1,5-dioxaspiro[5.5]undecane.
(10) 9-Aza-2-isopropyl-3,3,8,8,10,10-hexamethyl-1,5-dioxa-9-(2-propynyl)-spiro[5.5]undecane.
(11) 9-Aza-9-benzyl-3,3,8,8,10,10-hexamethyl-1,5-dioxa-spiro[5.5]undecane.
(12) 9-Aza-9-benzyl-3-ethyl-8,8,10,10-tetramethyl-1,5-dioxa-2-propyl-spiro[5.5]undecane.
(13) 9-Aza-9-(2-hydroxyethyl)-3,3,8,8,10,10-hexamethyl-1,5-dioxa-spiro[5.5]undecane.
(14) 9-Aza-9-(2-methoxyethyl)-3,3,8,8,10,10-hexamethyl-1,5-dioxa-spiro[5.5]undecane.
(15) 9-(2-Acetoxyethyl)-9-aza-3,3,8,8,10,10-hexamethyl-1,5-dioxa-spiro[5.5]undecane.
(16) 9-Aza-9-(2-methacryloyloxyethyl)3,3,8,8,10,10-hexamethyl-1,5-dioxa-spiro[5.-5]undecane.
(17) 9-Aza-3,3,8,8,10,10-hexamethyl-1,5-dioxa-9-(2-stearoyloxyethyl)-spiro[5.5]undecane.
(18) 9-Aza-9-(2-benzoyloxyethyl)-3,3,8,8,10,10-hexamethyl-1,5-dioxa-spiro[5.5]undecane.
(19) 9-Aza-9-(2-benzoyloxyethyl)-3-ethyl-8,8,10,10-tetramethyl-1,5-dioxa-2-propyl-spiro[5.-5]undecane.
(20) 9-Aza-9-cyanomethyl-3,3,8,8,10,10-hexamethyl-1,5-dioxa-spiro[5.5]undecane.
(21) 9-Aza-9-(2-chloroethyl)-3-ethyl-8,8,10,10-tetramethyl-1,5-dioxa-2-propyl-spiro[5.5]undecane.
(22) 9-Aza-9-(2,3-epoxypropyl)-3,3,8,8,10,10-hexamethyl-1,5dioxa-spiro[5.5]undecane
(23) 9-Aza-9-ethoxycarbonylmethyl-3,3,8,8,10,10-hexamethyl-1,5-dioxa-spiro[5.5]undecane.
(24) 9-Acetyl-9-aza-3-ethyl-8,8,10,10-tetramethyl-1,5-dioxa-2-propyl-spiro[5.5]undecane.
(25) 9-Acryloyl-9-aza-3,8,8,10,10-pentamethyl-1,5-dioxa-3-propyl-spiro[5.5]undecane.
(26) 9-Aza-9-butoxycarbonyl-2-isopropyl-3,3,8,8,10,10-hexamethyl-1,5-dioxa-spiro[5.5]undecane.
(27) 9-Aza-9-benzyloxycarbonyl-3,3,8,8,10,10-hexamethyl-1,5-dioxa-spiro[5.5]undecane.
(28) 9-Aza-2-isobutyl-4,8,8,10,10-pentamethyl-1,5-dioxaspiro[5.5]undecane.

The compounds of the invention can be prepared by means of the following reactions, which can be performed under per se known conditions:

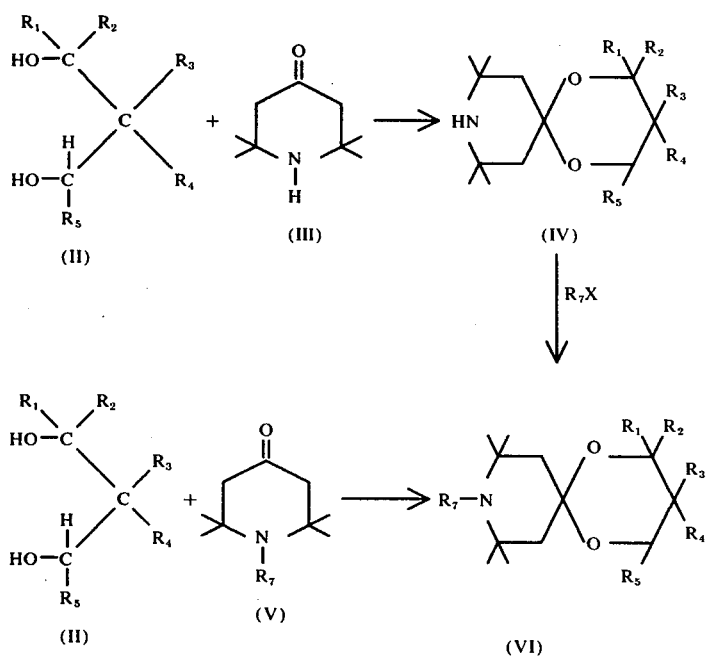

In these formulae, $R_1$, $R_2$, $R_3$, $R_4$ and $R_5$ are as defined above, $R_7$ is other than hydrogen atom but otherwise same with $R_6$ and X represents a halogen atom. In this reaction scheme, a trimethylene glycol derivative of formula (II) is reacted with triacetonamine (III) or a triacetonamine derivative (V) in the presence of an acidic catalyst (such as p-toluenesulphonic acid, sulphuric acid or hydrochloric acid), optionally in the presence of a solvent, with heating, thereby forming compound (IV) or compound (VI), respectively. Compound (VI) may also be obtained by reacting compound (IV) with a halide $R_7X$ in the presence of a basic acid-binding agent.

The piperidine derivatives of the invention are useful for stabilizing synthetic polymers against photo- and thermal-deterioration. Synthetic polymers which can be stabilized in this way include:

olefin, diene and styrene polymers
including homopolymers of olefins, dienes and styrene (e.g. low and high density polyethylenes, polypropylene, polystyrene, polybutadiene, and polyisoprene), and copolymers of olefins, dienes and styrene with each other or with other ethylenically unsaturated monomers (e.g. ethylene-propylene copolymers, ethylene-butene copolymers, ethylene-vinyl acetate copolymers, styrene-butadiene copolymers and acrylonitrile-butadiene-styrene copolymers);

vinyl chloride and vinylidene chloride polymers
including homopolymers of vinyl chloride and vinylidene chloride, vinyl chloride-vinylidene chloride copolymers, and copolymers of vinyl chloride or vinylidene chloride with vinyl acetate or with other ethylenically unsaturated monomers;

polyacetals e.g. polyoxymethylene and polyoxyethylene;

polyesters e.g. polyethylene terephthalate;

polyamides e.g. nylon-6, nylon-6,6, nylon-6,10 and nylon-12;

polyurethanes, and epoxy resins

The amount of stabilizers of formula (I) needed for effective stabilization of the synthetic polymer will depend on a variety of factors, such as the type and properties of the polymer concerned, its intended use, and the presence of other stabilizers. It is generally satisfactory to use from 0.01 to 5% by weight of the stabilizers of formula (I), based on the weight of the synthetic polymer, but the most effective range will vary with the type of polymer: viz 0.01 to 2.0%, preferably 0.02 to 1.0%, by weight for olefin, deiene and styrene polymers; 0.01 to 1.0%, preferably 0.02 to 0.5%, by weight for vinyl chloride and vinylidene chloride polymers, and 0.01% to 5.0%, preferably 0.02 to 2.0%, by weight for polyurethanes and polyamides. If desired, two or more of the stabilizers of formula (I) may be used together.

The stabilizers of formula (I) may readily be incorporated into the synthetic polymer by conventional techniques, at any convenient stage prior to the manufacture of shaped articles therefrom. For example, the stabilizer may be mixed with the synthetic polymer in dry powder form, or a suspension or emulsion of the stabilizer may be mixed with a solution, suspension, or emulsion of the synthetic polymer.

The stabilizers of the invention of formula (I) wherein 2 or 3 of $R_1$, $R_2$, $R_3$, $R_4$ and $R_5$ represent alkyl groups having from 1 to 4 carbon atoms have excellent compatibility with synthetic polymers, and particularly with polyolefins.

The stabilized synthetic polymer compositions of the invention may optionally also contain various conventional additives, such as the following:

Antioxidants

Simple, 2,6-dialkylphenols, such as, for example, 2,6-di-t-butyl-4-methylphenol, 2-t-butyl-4,6-dimethylphenol, 2,6-di-t-butyl-4-methoxymethylphenol and 2,6-dioctadecyl-4-methylphenol.

Derivatives of alkylated hydroquinones, such as, for example, 2,5-di-t-butylhydroquinone, 2,5-di-t-amylhydroquinone, 2,6-di-t-butylhydroquinone, 2,5-di-t-butyl-4-hydroxyanisole, 3,5-di-t-butyl-4-hydroxyanisole, tris(3,5-di-t-butyl-4-hydroxyphenyl)phosphite, 3,5-di-t-butyl-4-hydroxyphenylstearate and di-(3,5-di-t-butyl-4-hydroxyphenyl)adipate.

Hydroxylated thiodiphenyl ethers, such as, for example, 2,2'-thiobis(6-t-butyl-4-methylphenol), 2,2'-thiobis(4-octylphenol), 4,4'-thiobis-(6-t-butyl-3-methylphenol), 4,4'-thiobis(3,6-di-s-amylphenol), 4,4'-thiobis(6-t-butyl-2-methylphenol) and 4,4'-bis(2,6-dimethyl-4-hydroxyphenyl)disulphide.

Alkylidene-bisphenols, such as, for example, 2,2'-methylene-bis-(6-t-butyl-4-methylphenol), 2,2'-methylene-bis(6-t-butyl-4-ethylphenol), 4,4'-methylene-bis(6-t-butyl-2-methylphenol), 4,4'-methylene-bis-(2,6-di-t-butylphenol), 2,6-di-(3-t-butyl-5-methyl-2-hydroxybenzyl)-4-methylphenol, 2,2'-methylene-bis[4-methyl-6-($\alpha$-methylcyclohexyl)-phenol], 1,1-bis(3,5-dimethyl-2-hydroxyphenyl)butane, 1,1-bis(5-t-butyl-4-hydroxy-2-methylphenyl)butane, 2,2-bis(5-t-butyl-4-hydroxy-2-methylphenyl)butane, 2,2-bis(3,5-di-t-butyl-4-hydroxyphenyl)propane, 1,1,3-tris(5-t-butyl-4-hydroxy-2-methylphenyl)butane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane and ethylene glycol bis[3,3-bis(3'-t-butyl-4'-hydroxyphenyl)butyrate].

O-, N- and S-benzyl compounds, such as, for example, 3,5,3',5'-tetra-t-butyl-4,4'-dihydroxydibenzyl ether, 4-hydroxy-3,5-dimethylbenzyl-mercaptoacetic acid octadecyl ester, tri(3,5-di-t-butyl-4-hydroxybenzyl)amine, and bis(4-t-butyl-3-hydroxy-2,6-dimethylbenzyl)-dithiolterephthalate.

Hydroxybenzylate malonic esters, such as, for example, 2,2-bis(3,5-di-t-butyl-2-hydroxybenzyl)malonic acid dioctadecyl ester, 2-(3-t-butyl-4-hydroxy-5-methylbenzyl)malonic acid dioctadecyl ester, 2,2-bis(3,5-di-t-butyl-4-hydroxybenzyl)malonic acid di-dodecyl-mercaptoethyl ester, and 2,2-bis(3,5-di-t-butyl-4-hydroxybenzyl)-malonic acid di(4-t-octylphenyl)ester.

Hydroxybenzyl aromatics, such as, for example, 1,3,5-tri(3,5-di-t-butyl-4-hydroxybenzyl)-2,4,6-trimethylbenzene, 1,4-di(3,5-di-t-butyl-4-hydroxybenzyl)-2,3,5,6-tetramethylbenzene, and 2,4,6-tri-(3,5-di-t-butyl-4-hydroxybenzyl)phenol.

s-Triazine compounds, such as, for example, 2,4-bis-octylmercapto-6-(3,5-di-t-butyl-4-hydroxyanilino)-s-triazine, 2-octylmercapto-4,6-bis(3,5-di-t-butyl-4-hydroxyanilino)-s-triazine, 2-octylmercapto-4,6-bis(3,5-di-t-butyl-4-hydroxyphenoxy)-s-triazine, 2,4,6-tris(3,5-di-t-butyl-4-hydroxyphenoxy)-s-triazine, 2,4,6-tris(3,5-di-t-butyl-4-hydroxyphenylethyl)-s-triazine, and 1,3,5-tris(3,5-di-t-butyl-4-hydroxybenzyl)isocyanurate.

Amides of 3,5-di-t-butyl-4-hydroxyphenylpropionic acid, such as, for example, 1,3,5-tris(3,5-di-t-butyl-4- hydroxyphenyl-propionyl)-hexahydro-s-triazine, and N,N'-bis(3,5-di-t-butyl-4-hydroxypehnyl-propionyl)-hexamethylenediamine.

Esters of 3,5-di-t-butyl-4-hydroxyphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethyl isocyanurate, and 4-hydroxymethyl-1-phospha-2,6,7-trioxabicyclo[2,2,2]octane.

Esters of 5-t-butyl-4-hydroxy-3-methylphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethyl isocyanurate, and 4-hydroxymethyl-1-phospha-2,6,7-trioxabicyclo[2,2,2]octane.

Esters of 3,5-di-t-butyl-4-hydroxyphenylacetic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethyl-hexanediol, trimethylolethane, trimethylolpropane, trishydroxyethyl isocyanurate, and 4-hydroxymethyl-1-phospha-2,6,7-trioxabicyclo-[2,2,2]octane.

Acylaminophenols, such as for example, N-(3,5-di-t-butyl-4-hydroxyphenyl)stearic acid amide and N,N'-bis(3,5-di-t-butyl-4-hydroxyphenyl)thiobisacetamide.

Benzylphosphonates, such as, for example, 3,5-di-t-butyl-4-hydroxybenzylphosphonic acid dimethyl ester, 3,5-di-t-butyl-4-hydroxybenzyl-phosphonic acid diethyl ester, 3,5-di-t-butyl-4-hydroxybenzylphosphonic acid dioctadecyl ester, and 5-t-butyl-4-hydroxy-3-methylbenzylphosphonic acid dioctadecyl ester.

Aminoaryl derivatives, such as, for example, phenyl-1-naphthylamine, phenyl-2-naphthylamine, N,N'-diphenyl-p-phenylenediamine, N,N'-6-ethoxy-2,2,4-trimethyl-1,2-dihydroquinoline, 6-dodecyl-2,2,4-trimethyl-1,2-dihydroquinoline, mono-and di-octyliminodibenzyl, and polymerized 2,2,4-trimethyl-1,2-dihydroquinoline.

UV-absorbers and light protection agents 2-(2'-Hydroxyphenyl)benztriazoles, such as, for example, the 5'-methyl, 3',5'-di-t-butyl, 5'-t-butyl, 5'-(1,1,3,3-tetramethylbutyl), 5-chloro-3',5'-di-t-butyl, 5-chloro-3'-t-butyl-5'-methyl, 3'-s-butyl-5'-t-butyl, 3'-[α-methylbenzyl]-5'-methyl, 3'-[α-methylbenzyl]-5'-methyl-5-chloro, 4'-hydroxy, 4'-methoxy, 4'-octoxy, 3',5'-di-t-amyl, 3'-methyl-5'-carbomethoxyethyl and 5-chloro-3',5'-di-t-amyl derivatives.

2,4-Bis(2'-hydroxyphenyl)-6-alkyl-s-triazines, such as, for example, the 6-ethyl, 6-undecyl and 6-heptadecyl derivatives.

2-Hydroxybenzophenones, such as, for example, the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

1,3-Bis(2'-hydroxybenzoyl)benzenes, such as, for example, 1,3-bis (2'-hydroxy-4'-hexyloxybenzoyl)benzene, 1,3-bis(2'-hydroxy-4'-octoxybenzoyl)benzene and 1,3-bis(2'-hydroxy-4'-dodecyloxybenzoyl)-benzene.

Esters of optionally substituted benzoic acids, such as, for example, phenyl salicylate, octylphenyl salicylate, dibenzoylresorcinol, bis(4-t-butylbenzoyl)resorcinol, benzoylresorcinol and 3,5-di-t-butyl-4-hydroxybenzoic acid 2,4-di-t-butylphenyl ester, octadecyl ester or 2-methyl-4,6-di-t-butylphenyl ester.

Acrylates, such as, for example, α-cyano-β,β-diphenylacrylic acid ethyl ester or iso-octyl ester, α-carbomethoxycinnamic acid methyl ester, α-cyano-β-methyl-p-methoxycinnamic acid methyl ester or butyl ester, and N-(β-carbomethoxyvinyl)-2-methylindoline.

Nickel compounds, for example, nickel complexes of 2,2'-thiobis(4-t-octylphenol), such as the 1:1 and 1:2 complexes, optionally with other ligands such as n-butylamine, triethanolamine or N-cyclohexyldiethanolamine; nickel complexes of bis(4-t-octylphenyl)-sulphone, such as the 2:1 complex, optionally with other ligands such as 2-ethylcaproic acid; nickel dibutyldithiocarbamate; nickel salts of 4-hydroxy-3,5-di-t-butylbenzylphosphonic acid monoalkyl esters, such as the methyl, ethyl or butyl ester; the nickel complex of 2-hydroxy-4-methylphenyl undecyl ketonoxime; and nickel 3,5-di-t-butyl-4-hydroxybenzoate.

Oxalic acid diamides, such as, for example, 4,4'-dioctyloxyoxanilide, 2,2'-dioctyloxy-5,5'-di-t-butyloxanilide, 2,2'-di-dodecyloxy-5,5'-di-t-butyloxanilide, 2-ethoxy-5-t-butyl-2'-ethyloxanilide, 2-ethoxy-2'-ethyloxanilide, N,N'-bis(3-dimethylaminopropyl)oxalamide, mixtures of o- and p-methoxy and o-and p-ethoxy-di-substituted oxanilides, and mixtures of 2-ethoxy-5-t-butyl-2'-ethyloxanilide with 2-ethoxy-2'-ethyl-5,4'-di-t-butyloxanilide.

Metal deactivators, such as, for example, oxanilide, isophthalic acid dihydrazide, sebacic acid bisphenylhydrazide, bisbenzylidene oxalic acid dihydrazide, N,N'-diacetyladipic acid dihydrazide, N,N'-bis-salicyloyloxalic acid dihydrazide, N,N'-bis-salicyloylhydrazine, and N,N'-bis(3,5-t-butyl-4-hydroxyphenylpropionyl)hydrazine.

Phosphites, such as, for example, triphenyl phosphite, diphenyl alkyl phosphites, phenyl dialkyl phosphites, trinonyl phenyl phosphite, trilauryl phosphate, trioctadecyl phosphite, 3,9-di-isodecyloxy-2,4,8,10-tetraoxa-3,9-diphosphaspiro[5,5]undecane, and tris(4-hydroxy-3,5-di-t-butylphenyl)phosphite.

Peroxide deactivators, such as, for example, esters of β-thiodipropionic acid (e.g., the lauryl, stearyl, myristyl and tridecyl esters), salts of 2-mercaptobenzimidazole (e.g., the zinc salt), and diphenylthiourea.

Polyamide stabilizers, such as, for example, copper salts in combination with iodides and/or phosphorus compounds and salts of divalent manganese. melamine, benzoguanamine, triallyl cyanurate, dicyandiamide, urea derivative, hydrazine derivatives, amines, polyamides, polyurethanes, and alkali metal salts and alkaline earth metal salts of higher saturated or unsaturated fatty acids, (e.g. Ca stearate, Mg laurate, Na ricinoleate, K palmitate and Zn stearate).

PVC stabilizers, such as, for example, organic tin compounds, organic lead compounds and Ba/Cd salts of fatty acids.

Nucleating agents, such as, for example, 4-t-butylbenzoic acid, adipic acid, and diphenylacetic acid.

Other additives, such as, for example, plasticizers, lubricants, (e.g. glycerol monostearate), emulsifiers, antistatic agents, flameproofing agents, pigments, carbon black, asbestos, glass fibre, kaolin and talc.

The use of the stabilizers of formula (I) with the above-listed antioxidants is particularly effective for the stabilization of olefin polymers.

The invention is further illustrated by the following Examples in which all parts and percentages are by weight. Examples 1 to 4 illustrate the preparation of the piperidine derivatives of formula (I), whilst Examples 5 to 12 illustrate the stabilization of synthetic polymers, using compounds of the invention which are identified by means of the numbers appended to them in the list given hereinbefore.

EXAMPLE 1

9-Aza-3,3,8,8,10,10-hexamethyl-1,5-dioxa-spiro[5.5]undecane 104 g of 2,2-dimethyl-1,3-propanediol and 500 ml of toluene were added to 164 g of triacetonamine p-toluenesulphonate, and the mixture was refluxed for 15 hours while removing the water formed. After cooling, the reaction mixture was neutralized by the addition of 400 ml of a 30% aqueous sodium hydroxide solution and the mixture was stirred at room temperature. The toluene layer was then separated off and distilled under reduced pressure, giving the desired product as a colourless liquid boiling at 96°–98° C/0.4 mmHg. On cooling, the liquid crystallized to form colourless crystals melting at 30°–31° C.

Elementary analysis: Calculated for $C_{14}H_{27}NO_2$: C, 69.66%; H, 11.28%; N, 5.80%. Found: C, 69.98%; H, 11.38%; N, 6.06%.

IR spectrum (liquid film): the absorption of $\nu_{C=O}$ observed in the starting material was found to have dissipated and absorption of $\nu_{C-O}$ at 1,100 cm$^{-1}$ had appeared.

EXAMPLE 2

9-Aza-3,3,8,8,9,10,10-heptamethyl-1,5-dioxa-spiro[5.5]undecane 20 g of methyl iodide and 2.9 g of potassium carbonate were added to 10 g of the 9-aza-3,3,8,8,10,10-hexamethyl-1,5-dioxaspiro [5.5]undecane obtained in Example 1 and these materials were allowed to react, with stirring, at room temperature for 3 days. When the reaction was complete, a 10% aqueous potassium carbonate solution was added to the reaction mixture and the mixture was extracted with benzene. The benzene extract was dried over anhydrous potassium carbonate and then distilled under reduced pressure, giving the desired product as a colourless liquid boiling at 113–115° C/0.5 mmHg.

Elementary analysis: Calculated for $C_{15}H_{29}NO_2$: C, 70.54%; H, 11.45%; N, 5.48%. Found: C, 70.22%; H, 11.45%; N, 5.34%. NMR spectrum (CCl$_4$): τ7.79 (>N—CH$_3$, 3H).

EXAMPLE 3

9-Aza-9-benzyl-3,3,8,8,10,10-hexamethyl-1,5-dioxaspiro[5.5]undecane 20 g of benzyl bromide and 3.5 g of potassium carbonate were added to 12 g of 9-aza-3,3,8,8,10,10-hexamethyl-1,5-dioxaspiro [5.5]undecane (obtained in Example 1) and the mixture was heated at 100°–105° C, with stirring, for 7 hours. After cooling, a 10% aqueous potassium carbonate solution was added to the reaction mixture and the mixture was extracted with benzene. The benzene solution was concentrated and the resulting crystals were then recrystallized from n-hexane, giving the desired product as colourless crystals melting at 94–95° C.

Elementary analysis: Calculated for $C_{21}H_{33}NO_2$: C, 76.09%; H, 10.03%; N, 4.23%. Found: C, 76.04%; H, 9.98%; N, 4.44%. NMR spectrum (CCl$_4$): τ6.15 (>N—CH$_2$—, 2H).

EXAMPLE 4

9-Aza-3,3,8,8,9,10,10-heptamethyl-1,5-dioxa-spiro[5.5]undecane 20.8 g of 2,2-dimethyl-1,3-propanediol and 200 ml of toluene were added to 34.1 g of N-methyl-triacetonamine p-toluenesulphonate and the mixture was allowed to react. After following substantially the same procedure as is described in Example 1, the desired product was obtained as a colourless liquid boiling at 113–115° C/0.5 mmHg.

Elementary analysis: Calculated for $C_{15}H_{29}NO_2$: C, 70.54%; H, 11.45%; N, 5.48%. Found: C, 70.73%; H, 11.56%; N, 5.66%.

The IR spectrum (liquid film) and NMR spectrum (CCl$_4$) of this compound coincided exactly with those of the compound obtained in Example 2.

The following compounds were synthesized by the procedures of Examples 1 to 4:
- 9-aza-2,4,4,8,8,10,10-heptamethyl-1,5-dioxaspiro [5.5]undecane, bp 88–90° C/0.3 mmHg;
- 9-aza-3,8,8,10,10-pentamethyl-1,5-dioxa-3-propyl-spiro [5.5]undecane, bp 120 – 121° C/0.3 mmHg;
- 9-aza-2-isopropyl-3,3,8,8,10,10-hexamethyl-1,5-dioxa-spiro [5.5]undecane, bp 114 – 117° C/0.3 mmHg;
- 9-aza-3-ethyl-8,8,10,10-tetramethyl-1,5-dioxa-2-propyl-spiro [5.5]undecane, bp 119 – 121° C/0.2 mmHg;
- 9-allyl-9-aza-3,3,8,8,10,10-hexamethyl-1,5-dioxa-spiro [5.5]undecane, bp 120°–121° C/0.25 mmHg;
- 9-aza-9-benzyl-3,3,8,8,10,10-hexamethyl-1,5-dioxa-spiro [5.5]undecane, mp 94°– 95° C;
- 9-aza-9-(2-hydroxyethyl)-3,3,8,8,10,10-hexamethyl-1,5-dioxa-spiro [5.5]undecane, mp 82°– 84° C;
- 9-aza-9-(2-methoxyethyl)-3,3,8,8,10,10-hexamethyl-1,5-dioxa-spiro [5.5]undecane, bp 95° –98° C/0.15 mmHg;
- 9-(2-acetoxyethyl)-9-aza-3,3,8,8,10,10-hexamethyl-1,5-dioxa-spiro [5.5]undecane, bp 158° –162° C/0.3 mmHg;
- 9-aza-9-(2-benzoyloxyethyl)-3,3,8,8,10,10-hexamethyl-1,5-dioxa-spiro[5.5]undecane, mp 123° –125° C;
- 9-aza-9-cyanomethyl-3,3,8,8,10,10-hexamethyl-1,5-dioxa-spiro [5.5]undecane, mp 110° –112° C;
- 9-aza-9-ethoxycarbonylmethyl-3,3,8,8,10,10-hexamethyl-1,5-dioxa-spiro [5.5]undecane, bp 152 – 155° C/0.3 mmHg;
- 9-aza-9-benzyl-3-ethyl-8,8,10,10-tetramethyl-1,5-dioxa-2-propyl-spiro [5.5]undecane, bp 192° – 194° C/0.5 mmHg;
- 9-aza-9-(2, 3 -epoxypropyl)-3,3,8,8,10,10-hexamethyl- 1,5-dioxa-spiro[5.5]undecane, bp 160° –162° C/0.5 mmHg;
- 9-acetyl-9-aza-3-ethyl-8,8,10,10-tetramethyl-1,5-dioxa-2-propyl-spiro [5.5]undecane, bp 171° – 173° C/0.5 mmHg;

9-aza-9-benzyloxycarbonyl-3,3,8,8,10,10-hexamethyl-1,5-dioxa-spiro[5.5]undecane, bp 185° –190° C/0.3 mmHg.

EXAMPLE 5

Mixtures were made from 100 parts of polypropylene ("Noblen JHH-G", available from Mitsui Toatsu Chemicals Inc., employed after two recrystallizations from monochlorobenzene) and 0.25 part of each in turn of the stabilizers of the invention indicated in Table 1. The resulting mixtures were blended, melted and moulded under heating and pressure into sheets 0.5 mm thick. A control sheet, containing no stabilizer, was also made.

The sheets thus formed were exposed to ultraviolet irradiation at 45° C in the "Standard Fade-Meter Type FA-1" manufactured and sold by Toyo Rika Instruments Inc., Japan (a modification of the Atlas Fade-O-Meter Type FDA-R, which meets the requirements prescribed in paragraph 3.8 of Japanese Industrial Standard 1044-L). The time required for each sheet to become brittle was measured and is shown in Table 1.

EXAMPLE 6

Mixtures were made from 100 parts of high-density polyethylene ("Hi-Zex", available from Mitsui Toatsu Chemicals Inc., Japan, employed after two recrystallizations from toluene) and 0.25 part of each in turn of the stabilizers of the invention indicated in Table 1. The resulting mixtures were moulded under heating and pressure into sheets 0.5 mm thick. A control sheet containing no stabilizer was also made. The time required for each sheet to become brittle was measured by the same method as in Example 5, and the results are shown in Table 1.

Table 1

| Stabilizer No. | Brittleness time (hours) | |
|---|---|---|
| | Polypropylene | High-density polyethylene |
| 1 | 660 | 1380 |
| 4 | 600 | 1240 |
| 5 | 620 | 1280 |
| 6 | 640 | 1300 |
| 9 | 620 | 1360 |
| 11 | 660 | 1280 |
| 13 | 660 | 1220 |
| 15 | 540 | 1020 |
| 18 | 580 | 1060 |
| 20 | 640 | 1240 |
| 23 | 660 | 1340 |
| None | 60 | 380 |

EXAMPLE 7

Mixtures were made from 100 parts of polystyrene ("Styron", available from Asahi-Dow Limited, Japan, employed after recrystallization from a mixture of benzene and methanol) and 0.25 part of each in turn of the stabilizers of the invention indicated in Table 2. The resulting mixtures were moulded at 180° C under pressure into sheets 1 mm thick. A control sheet containing no stabilizer was also made.

The sheets thus formed were exposed to ultraviolet irradiation for 500 hours at 45° C in the Fade-Meter described in Example 5. The difference in colour before and after the exposure to ultraviolet irradiation was measured in test pieces of the sheets by the method prescribed in Japanese Industrial Standard K-7103, using a colour-difference colourimeter; and the change in their yellowness index was calculated by means of the equation:

$$\Delta YI = YI - YI_0$$

wherein $\Delta YI$ is the change in yellowness index, $YI$ is the yellowness index after exposure, and $YI_0$ is the initial yellowness of the test piece.

The results are shown in Table 2.

Table 2

| Stabilizer No. | $YI_0$ | $\Delta YI$ |
|---|---|---|
| 1 | 4.9 | +3.2 |
| 6 | 4.6 | +3.0 |
| 11 | 4.2 | +2.9 |
| 18 | 4.3 | +2.9 |
| None | 4.7 | +16.3 |

EXAMPLE 8

Mixtures were made from 100 parts of acrylonitrile-butadienestyrene resin ("Kane Ace B-12", available from Kanegafuchi Chemical Industries Co. Limited, Japan) and 0.5 part of each in turn of the stabilizers of the invention inindicated in Table 3. The resulting mixtures were kneaded for 6 minutes on kneading rolls at 160° C, and then moulded into sheets about 0.5 mm thick. A control sheet containing no stabilizer was also made.

The sheets thus formed were exposed for 50 hours in the "Sunshine Weather-Ometer", prescribed in Japanese Industrial Standard Z-0230, entitled "Accelerated Weathering Test of Rustproofing Oils", paragraph 2. The retention of ultimate elongation and of ultimate tensile strength as well as the degree of coloration of the sheets were then measured by a standard method.

The results are shown in Table 3.

Table 3

| Stabilizer No. | Retention of elongation (%) | Retention of tensile strength (%) |
|---|---|---|
| 9 | 68 | 78 |
| 11 | 70 | 81 |
| 18 | 73 | 77 |
| None | 53 | 69 |

EXAMPLE 9

Mixtures were made from 100 parts of nylon-6 ("CM1011, " available from Toray Industries Inc., Japan) and 0.25 part of each in turn of the stabilizers of the invention indicated in Table 4. The resulting mixtures were melted and moulded under pressure into films about 0.1 mm thick, using a conventional compression moulding machine. A control film containing no stabilizer was also made.

The films thus formed were aged under the conditions described below, and their retention of ultimate tensile strength and of ultimate elongation were then measured by a standard method. The results are shown in Table 4.

Ageing conditions (1) Exposure to ultraviolet irradiation for 200 hours at 45° C in the Fade-Meter described in Example 5.

(2) Ageing at 160° C for 2 hours in the Geer's ageing tester prescribed in Japanese Industrial Standard K-6301 entitled "Physical Testing Methods for Vulcanized Rubber," paragraph 6.5

Table 4

| Stabilizer No. | Fade-Meter | | Geer's ageing tester | |
| --- | --- | --- | --- | --- |
| | retention of elongation (%) | retention of tensile strength (%) | retention of elongation (%) | retention of tensile strength (%) |
| 6 | 69 | 73 | 74 | 78 |
| 11 | 71 | 73 | 72 | 79 |
| 18 | 72 | 75 | 73 | 75 |
| None | 19 | 50 | 18 | 53 |

EXAMPLE 10

Mixtures were made from 100 parts of polycaprolactone-type polyurethane ("E-5080", available from Nippon Elastollan Industries Limited, Japan) and 0.5 part of each in turn of the stabilizers of the invention indicated in Table 5. The resulting mixtures were melted and moulded into sheets about 0.5 mm thick. A control sheet containing no stabilizer was also made.

The sheets thus formed were exposed to ultraviolet irradiation for 15 hours at 45° C in the Fade-Meter described in Example 5, and their retention of ultimate elongation and of ultimate tensile strength were then measured by a standard method.

The results are shown in Table 5.

Table 5

| Stabilizer No. | Retention of elongation (%) | Retention of tensile strength (%) |
| --- | --- | --- |
| 1 | 84 | 89 |
| 6 | 87 | 90 |
| 11 | 86 | 91 |
| 23 | 82 | 83 |
| None | 74 | 52 |

EXAMPLE 11

Mixtures were made from 100 parts of polyvinyl chloride resin ("Geon 103EP", available from the Nippon Geon Co. Limited, Japan), 3 parts of dibutyltin maleate, 0.5 part of butyl stearate and 0.25 part of each in turn of the stabilizers of the invention indicated in Table 6. The resulting mixtures were kneaded for 5 minutes on kneading rolls at 180° C, and formed into sheets 0.5 mm thick. A control sheet, containing none of the stabilizers of the invention, was also made.

The sheets thus formed were exposed for 300 hours to the Sunshine Weather-Ometer described in Example 8, and their degree of discloration was noted. The results are shown in Table 6.

Table 6

| Stabilizer No. | Colour |
| --- | --- |
| 1 | Pale brown |
| 9 | Pale brown |
| 11 | Pale brown |
| None | Dark brown |

EXAMPLE 12

Mixtures were made from 100 parts of polyester resin ("Ester-G13", available from Mitsui Toatsu Chemicals Inc., Japan), 1 part of benzoyl peroxide, and 0.2 part of each in turn of the stabilizers of the invention indicated in Table 7. The resulting mixtures were cured by preheating at 60° C for 30 minutes and then heated at 100° C for 1 hour, to form sheets 3 mm thick. A control sheet, containing none of the stabilizers of the invention, was also made.

The sheets thus formed were irradiated for 60 hours in the Sunshine Weather-Ometer described in Example 8, and the change in their yellowness index was determined by the method described in Example 7. The results are shown in Table 7.

Table 7

| Stabilizer No. | $YI_0$ | $\Delta YI$ |
| --- | --- | --- |
| 9 | 2.4 | +8.9 |
| 11 | 2.3 | +8.7 |
| 18 | 2.2 | +8.1 |
| None | 1.8 | +13.1 |

We claim:

1. An improved polymer composition of the type comprising a synthetic polymer and a stabilizer therefor, the improvement comprising using as stabilizer at least one compound of formula:

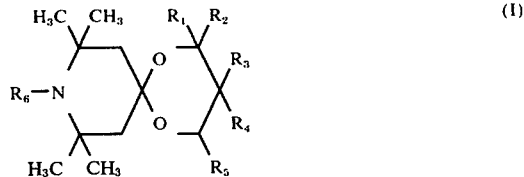

(I)

wherein:
   2 or 3 of $R_1$, $R_2$, $R_3$, $R_4$ and $R_5$ represent alkyl groups having from 1 to 4 carbon atoms, and the remainder of $R_1$, $R_2$, $R_3$, $R_4$ and $R_5$ represent hydrogen atoms; and $R_6$ is selected from the group consisting of: a hydrogen atom, alkyl groups, alkenyl groups, alkynyl groups, aralkyl groups, hydroxyalkyl groups, alkoxyalkyl groups, aliphatic and aromatic acyloxyalkyl groups, cyanoalkyl groups, haloalkyl groups, epoxyalkyl groups, alkoxycarbonylalkyl groups, aliphatic acyl groups, alkoxycarbonyl groups and aralkoxycarbonyl groups.

2. A composition as claimed in claim 1, wherein there is used from about 0.01 to about 5% by weight of said stabilizer 3. A composition as claimed in claim 1, wherein the synthetic polymer is selected from the group consisting of olefin, diene and styrene polymers.

4. A composition as claimed in claim 2, wherein the synthetic polymer is selected from the group consisting of monoolefin, conjugated diene and styrene polymers.

5. A composition as claimed in claim 1, wherein the synthetic polymer is selected from the group consisting of vinyl chloride and vinylidene chloride polymers.

6. A composition as claimed in claim 1, wherein the synthetic polymer is selected from the group consisting of polyacetals, polyesters, polyester ethers, polyamides, polyurethanes and epoxy resins.

* * * * *